United States Patent
Russell-Jones et al.

(10) Patent No.: US 6,221,397 B1
(45) Date of Patent: Apr. 24, 2001

(54) SURFACE CROSS-LINKED PARTICLES SUITABLE FOR CONTROLLED DELIVERY

(75) Inventors: Gregory J. Russell-Jones, Middle Cove; Scott M. Starling, Bexley; John F. McEwan, Oatley, all of (AU)

(73) Assignee: Biotech Australia PTY Limited, Roseville (AU)

(*) Notice: Subject to any disclaimer, the term of this patent is extended or adjusted under 35 U.S.C. 154(b) by 0 days.

(21) Appl. No.: 09/143,118

(22) Filed: Aug. 28, 1998

(30) Foreign Application Priority Data

Aug. 29, 1997 (AU) .............................. PO8880/97

(51) Int. Cl.⁷ .............................. A61K 9/14; A61K 39/00; A61K 9/50
(52) U.S. Cl. .................. 424/486; 424/489; 424/484; 424/499; 424/501
(58) Field of Search .................. 424/488, 489, 424/490, 484, 486, 499, 501; 514/951

(56) References Cited

U.S. PATENT DOCUMENTS

| | | |
|---|---|---|
| 5,284,936 | 2/1994 | Donachy et al. .................. 530/350 |
| 5,449,720 | * 9/1995 | Russell-Jones et al. . |
| 5,487,895 | * 1/1996 | Dapper et al. . |
| 5,534,259 | * 7/1996 | Zalipsky et al. . |
| 5,548,064 | * 8/1996 | Russell-Jones et al. . |
| 5,674,531 | * 10/1997 | Ahlers et al. . |

FOREIGN PATENT DOCUMENTS

| | | |
|---|---|---|
| 54638/96 | 8/1996 | (AU) . |
| WO 95/05162 | 2/1995 | (WO) . |
| WO 97/49387 | 12/1997 | (WO) . |
| WO 99/11703 | 3/1999 | (WO) . |

OTHER PUBLICATIONS

Xu et al., Preparation and in vitro Activity of Monoclonal Antibody–pharmorubicin Immunoconjugates, Acta Pharmaceutica Sinica, vol. 31, No. 8, pp. 632–636, 1996.*
Abstract JP 2–235902, "Porous granules for chromatography—comprises cellulose (deriv.) with xanthite crosslinkage"., Sep. 1990.

* cited by examiner

Primary Examiner—Thurman K. Page
Assistant Examiner—Brian K. Seidleck
(74) Attorney, Agent, or Firm—Foley & Lardner

(57) ABSTRACT

Cross-linked particles are provided that are useful for delivery of pharmaceutical agents. The particles comprise at least one polymeric compound and a spacer compound, where the polymeric compound and the spacer each comprise reactive carboxyl, hydrazidyl, amino and/or thiol groups. The particles are cross-linked via covalent linkage of the reactive groups on the polymer and spacer respectively. Compositions comprising pharmaceutical agents contained within the particles are disclosed. Methods for preparing the particles, for encapsulating pharmaceutical agents within the particles, and for using the particles for controlled release of the pharmaceutical agent within the patient also are provided.

29 Claims, 5 Drawing Sheets

IV ADMINISTRATION OF AH-CMC/GEL NANOPARTICLES −+ AEABE

FIG. 5

MODIFICATION OF SERUM GLUCOSE BY ORAL IBCA NPs

SURFACE CROSS-LINKED PARTICLES SUITABLE FOR CONTROLLED DELIVERY

FIELD OF THE INVENTION

The present invention relates to cross-linked particles useful for pharmaceutical delivery. In particular, the invention relates to improved methods of stabilizing such particles and controlling uptake and pharmaceutical agent release within a vertebrate host.

BACKGROUND OF THE INVENTION

The effective delivery of a pharmaceutical agent to an active site and achieving an acceptable rate of release of pharmaceutical agents are enduring problems in developing and improving pharmaceutical therapies. In particular, it is well recognized that the gastro-intestinal tract of vertebrate animals provides a number of physical and chemical barriers against the successful administration of therapeutic agents. For example a therapeutic agent must be able to withstand the attack of endogenous enzymes, gastric acidity and intestinal alkalinity without losing activity, and then still penetrate across the gastrointestinal mucosa, into the blood stream and to the site where activity is required. Moreover, all of this must take place at an appropriate rate to ensure the correct therapeutic dosage is delivered.

In the past, many approaches have been adopted to attempt to solve these problems. For example, administration of a particularly high dose of active agent can be effective in ensuring that at least some of the agent reaches the desired active site without degradation. This approach to administration of enteric agents is clearly problematic and not economical. In some instances it can be appropriate for simple mechanical carriers such as pressed tablets or enteric coatings to be provided in order to improve enteric tolerance of the agent concerned, and to regulate the rate of drug release. There has also been considerable research recently to develop liposomes or lipid microbubbles that can be used to encapsulate active agents. These approaches have not been successful in all circumstances.

Micro and nanoparticles which can encapsulate pharmaceutical agents in order to provide protection and regulate their rate of release were described in U.S. Pat. No. 5,352,461. This patent relates to the self-assembling particle drug delivery systems formed from 2,5-diketo-3,6-di(4-succinylaminobutyl)piperazine, which are claimed to be pH sensitive so that they therefore disassemble and release the entrapped pharmaceutical agent, at high pH. Other particles which are suggested as being able to encapsulate agents such as insulin and heparin and protect these molecules from gastric acidity and stomach enzymes, and to release the agents into the bloodstream, were proposed in International Patent Publication No. WO 88/01213. Self-assembling pH titratable particulate systems, based upon the self-assembling properties of bis-amide dicarboxylic acids are described in the work of Bergeron et al., *J. Amer. Chem. Soc.* 1995, 117, 6658–6665. These particles also share the properties of stability at low pH and instability as pH increases.

International Patent Publication No. WO 96/29991 describes the formation of self-assembling particles that are based upon polyaminoacids, more particularly polyleucineglutamate. These particles which are prepared from natural amino acids have the property of controlled particle size and are stable over a wide pH range.

Particles for entrapment of pharmaceutical agents, and particularly peptides or proteins, can also be formed by polyelectrolyte complexation of various anionic polymers with cationic polymers. Anionic polymers may include natural substances such as sodium alginate, carboxymethyl cellulose, guaran, polyglutamic acid and their derivatives, amongst others. Examples of cationic polymers include polylysine and gelatin. Other polycations and polyanions are described in detail within European Patent No. 671169, U.S. Pat. Nos. 4,835,248 and 5,041,291, which are incorporate herein by reference in their entirety.

Unfortunately, there are limitations to the effectiveness of particles for pharmaceutical delivery according to the prior art, as it has been found in many cases that these particles rapidly release the entrapped pharmaceutical agent upon parenteral or enteral administration. As a result, efforts have been made to develop stabilised microparticles by the use of glutaraldehyde cross-linking. This method of cross-linking however suffers from the disadvantage that it can result in the modification of the entrapped pharmaceutical agent, which is clearly undesirable. A further disadvantage is that such cross-linking is optimally performed under alkaline conditions, the same conditions under which many of these pH-sensitive particles will rapidly release the entrapped pharmaceutical agents.

It is apparent, therefore, that practical methods of particle stabilisation that are suitable for use with pH-sensitive particles and which can be performed with little or no risk of modification of the entrapped pharmaceutical agent are greatly to be desired. In particular, methods that can be used for delivery of pharmaceutical agents are highly desirable.

SUMMARY OF THE INVENTION

It is therefore an object of the present invention to provide practical methods of particle stabilization which reduce or eliminate modification of an entrapped pharmaceutical agent.

It is a further object of the present invention to provide methods for delivering pharmaceutical agents that reduce or eliminate modification of the pharmaceutical agent.

In accomplishing the foregoing objects, there have been provided, in accordance with one aspect of the present invention, cross-linked particles which can be formulated using the following components:

a) one or more polymers capable of forming a particle, each comprising reactive carboxyl, hydrazidyl, amino and/or thiol groups; and b) a spacer comprising two or more reactive carboxyl, hydrazidyl, amino and/or thiol groups groups;

wherein cross-linking is achieved by carbodiimide linkage between the carboxyl group and the hydrazidyl, amino and/or thiol groups of the polymer(s) and the spacer.

According to another embodiment of the present invention there is provided a composition comprising a pharmaceutical agent entrapped within a cross-linked particle, wherein the cross-linked particle comprises:

a) one or more polymers capable of forming a particle, each comprising reactive carboxyl, hydrazidyl, amino and/or thiol groups groups; and b) a spacer comprising two or more reactive carboxyl, hydrazidyl, amino and/or thiol groups groups; and wherein cross-linking is achieved in the presence of the pharmaceutical agent and is catalyzed by carbodiimide linkage between the carboxyl group and the, hydrazidyl, amino and/or thiol groups of the polymer(s) and the spacer.

According to a further embodiment of the present invention there is provided a method of producing a cross-linked particle which comprises reacting, under appropriate conditions:

a) one or more polymers capable of forming a particle, each comprising reactive carboxyl, hydrazidyl, amino and/or thiol groups; and b) a spacer comprising two or more reactive carboxyl, hydrazidyl, amino and/or thiol groups; and;

wherein cross-linking is achieved by carbodiimide linkage between the carboxyl group and the hydrazidyl, amino and/or thiol groups of the polymer/s and the spacer.

According to another embodiment of the present invention there is provided a method of producing a composition containing one or more pharmaceutical agents, comprising reacting a cross-linked particle with one or more pharmaceutical agents, wherein the particle comprises a) one or more polymers capable of forming a particle, each comprising reactive carboxyl, hydrazidyl, amino and/or thiol groups;

b) a spacer comprising two or more reactive carboxyl, hydrazidyl, amino and/or thiol groups; and wherein cross-linking is achieved by carbodiimide linkage between the carboxyl group and the hydrazidyl, amino and/or thiol groups of the polymer/s and the spacer.

According to still another embodiment of the present invention there is provided a method of controlled pharmaceutical agent release in a patient, comprising administering to said patient an effective amount of a composition comprising a pharmaceutical agent entrapped within a cross-linked particle, wherein said particle comprises:

a) one or more polymers capable of forming an encapsulating particle, each comprising reactive carboxyl, hydrazidyl, amino and/or thiol groups; and b) a spacer comprising two or more reactive carboxyl, hydrazidyl, amino and/or thiol groups.

In these embodiments, the spacer preferably has the formula:

$NH_2NHCO-R-CONHNH_2$, where —R— is a direct bond, or R is a straight, branched chain or cyclic alkyl, alkenyl, alkynyl or aryl group, and where the alkyl, alkenyl, or alkynyl group contains up to 10 carbon atoms. The spacer also may be selected from the group consisting of: hydrazine, oxalic dihydrazide, malonic dihydrazide, succinic dihydrazide, glutaric dihydrazide, adipic dihydrazide, maleic dihydrazide, fumaric dihydrazide or butadienoic dihydrazide, glutamic dihydrazide, aspartic dihydrazide, malic dihydrazide, tartaric dihydrazide, terephthalic dihydrazide, isophthalic dihydrazide, and phthalic dihydrazide.

In further embodiments, the spacer may be selected from the group consisting of malonic acid, maleic acid, malic acid, citric acid, glutamic acid, aspartic acid, succinic acid, adipic acid, glutaric acid, dimethylglutaric acid, oxalic acid, fumaric acid, phthalic acid, tartaric acid, isophthalic acid, and terephthalic acid and the branched alkyl derivatives thereof, wherein the alkyl group of said alkyl derivatives contains up to 10 carbon atoms.

In still further embodiments, the spacer comprises at least one reactive carboxyl group and at least one reactive hydrazidyl group. The spacer also may comprise at least one biodegradable linkage. The biodegradable linkage may be an ester linkage, for example where the spacer is a 2-aminoethyl ester of an amino acid. In a preferred embodiment, the spacer is a 2-aminoethyl ester of glycine or phenylalanine, or a disuccinimidyl derivative thereof. In a preferred embodiment, the disuccinimidyl derivatives of the 2-aminoethyl esters of glycine and phenylalanine are selected from the group consisting of N,N'-disuccinimidyl-(2-amino-2-benzyl-ethanoate), N,N'-dissuccinimidyl-2-amino-ethyl-ethanoate, and ethylene glycolbis[succinimidylsuccinate]

The cross-linked particle may be covalently bound to a targeting compound. In other embodiments, the pharmaceutical agent is selected from the group consisting of peptide and protein pharmaceuticals, DNA, RNA,), antibodies, vaccines, imaging agents, hormones, polysaccharides, antibiotics, anticoagulants, immunomodulating agents, cytotoxic agents, steroids, decongestants, anesthetics and sedatives. In preferred embodiments, the pharmaceutical agent is selected from the group consisting of calcitonin, erythropoietin, thrombopoietin, granulocyte colony stimulating factor, stem cell factor, LHRH analogs, somatostatin, insulin, interferons and plasminogen activator inhibitors.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Cross-linked particles are provided that are useful for delivering pharmaceutical agents that otherwise would experience a loss of efficacy as a result of instability, inadequate uptake, or an inappropriate rate of release. In particular, the pharmaceutical agents comprehended by the present invention include peptide and protein pharmaceuticals which are subject to proteolytic degradation or are otherwise unstable in the stomach and small intestine.

In general, the preferred method for administration of therapeutic agents is via an enteric, and particularly oral, route. This provides ease of administration and an associated high level of patient compliance. However, many therapeutic agents currently cannot be effectively delivered via an oral route. Examples of such agents include peptide and protein pharmaceuticals include calcitonin, erythropoietin, thrombopoietin, granulocyte colony stimulating factor, stem cell factor, LHRH analogs, somatostatin, insulin, interferons, plasminogen activator inhibitors, recombinant antibodies and monoclonal antibodies. In the context of the present invention, the term "pharmaceutical agent" is not in any way limited to peptide and protein pharmaceuticals, but includes any therapeutic, prophylactic or diagnostic agent whose delivery may be aided by using the cross-linked particles according to the present invention. For example, delivery of species of DNA and RNA (sense or antisense), antibodies, vaccines as well as more traditional chemotherapeutic agents is contemplated. Thus, the term "pharmaceutical agent" is to be understood as encompassing simple organic or inorganic compounds, nutritional agents and imaging agents such as metals, radioactive isotopes, radio-opaque or radiolucent agents. Examples of "traditional" chemotherapeutic agents include hormones, polysaccharides, such as heparin, antibiotics, anti-inflammatory compounds, antivirals, vasoactiv- and neuroactive agents, anticoagulants, immunomodulating agents, cytotoxic agents, steroids, decongestants, anaesthetics, sedatives and any other agents required to be delivered to a patient for therapeutic, prophylactic or diagnostic purposes. This list of classes of pharmaceutical agents is not intended to be exhaustive.

In addition, the pharmaceutical agents according to the invention can occur in various forms, for example as charged or uncharged molecules, as components of molecular complexes, as salts, amines, ethers, esters, or amides, or as other derivatives or pro-drugs of the agents concerned.

The present invention is not limited to enteric delivery of pharmaceutical agents. For example, parenteral delivery of pharmaceutical agents can also benefit from the present invention, such as when a pharmaceutical agent must penetrate barriers (other than the gastrointestinal mucosa) within the body in order to reach the target organ or target site. The blood-brain barrier is one example of such a barrier. In addition, a pharmaceutical agent may be delivered to, and retained at, a particular active site.

In the context of the present invention, the term "cross-linked" indicates that covalent chemical linkages are introduced within and/or between the polymers that comprise the particle. This cross-linking increases the stability of the particle, thereby providing better protection to the entrapped pharmaceutical agent, as well as improving the level of control that can be exerted over the timing and rate of pharmaceutical agent release.

The cross-linking techniques according to the present invention can be applied to any type of particle that either is already known, or that may be devised in the future, provided that the polymer components of the particle either comprise, or can be modified to comprise, reactive carboxyl, hydrazidyl, amino and/or thiol groups. The term "reactive" in this context indicates that these groups are present preferably on an external surface of the particle, and are not hindered by other functional groups, thereby allowing the cross-linking reactions comprehended by the present invention to occur.

The term "particle" also encompasses all particles for pharmaceutical agent delivery irrespective of their 3-dimensional shape or conformation. The particles of the invention may be such that they fully or partially encapsulate the pharmaceutical agent or entrap the pharmaceutical agent within the polymer matrix of the particle. Particles previously classified as either micro- or nanoparticles are included within this definition, so that average particle diameter may vary from between about 10 nm and 900 $\mu$m. For example, particles intended to act as implants which will be localised in a particular area of the body for controlled release of the pharmaceutical agent may appropriately have average diameter of 400–800 $\mu$m, whereas particles requiring internalisation by cells or transport across the gastrointestinal mucosa will have average diameter less than about 10 $\mu$m. In contrast, particles administered subcutaneously may appropriately be larger than 10 $\mu$m in average diameter to prevent the particles re-entering the general circulation.

The shape and 3-dimensional conformation of the particle used will depend on the intended utility of the particle concerned. Specifically, particle shape or conformation may be chosen based upon knowledge of the 3-dimensional shape or conformation of the pharmaceutical agent that is to be delivered.

The following documents, which are incorporated herein by reference in their entirety, refer to various types of particles that can be used or modified for use in relation to the present invention. This list of documents and the types of particles disclosed therein is not intended to be exhaustive. U.S. Pat. No. 5,352,461; International Patent Publication No. WO 88/01213; Bergeron et al., *J. Am. Chem. Soc.*, 1995, 117, 6658–6665; International Patent Publication No. WO 96/29991; European Patent No. 6712169; and U.S. Pat. Nos. 4,835,248; and 5,041,291.

In general terms, and again without limiting the intended scope of the invention in any way, particles for delivery of pharmaceutical agents can be formed via a number of methods, several of which are outlined below:

(i) Solvent Evaporation

In this technique a compound which is soluble in one solvent is dispersed into a non-miscible solvent and the first solvent is evaporated off. Particles formed in this fashion have been used to administer parenterally a number of water insoluble compounds. An example of such a system would be the formation of polylactic-glycolic acid nanoparticles in which the antifungal agent, griseofulvin is entrapped.

(ii) Desolvation

In this method a compound is dissolved in a first liquid (the solvent) and a second liquid (which is miscible with the first liquid, but in which the compound is not soluble) is added to the solvent. As more of the second liquid is added the compound becomes desolvated. During the process of desolvation the compound rich phase (the coacervate) contains an enriched amount of compound which is dispersed as microdroplets in the compound deficient phase. At this stage the coalesced material can be chemically cross-linked by a suitable cross-linking agent to form micro- or nanoparticles. Nanoparticles of gelatin or BSA can be prepared in this way. Solutions of these proteins are desolvated by the addition of sodium sulfate, or ammonium sulfate solutions. At the point of desolation there is an increase in turbidity, at which time the nanoparticles can be formed by the addition of a suitable cross-linker such as glutaraldehyde or butanedione.

(iii) Complex Coacervation

In this procedure two polyelectrolytes having opposite charge are mixed in aqueous medium so that a spontaneous liquid/liquid phase separation occurs. The phenomenon is limited to polymers having a suitable ionic charge density and chain length. Typically these microspheres are formed by the addition of a polyanion such as polyglutamic acid, carboxymethyl cellulose, gum Arabic, alginate, or polyphosphate, to a polycation such as gelatin or polylysine.

(iv) Polymer/Polymer Incompatibility

This procedure is based upon the observation that two chemically different polymers dissolved in a common solvent usually are incompatible. Thus the mixture will tend to form two phases. The insoluble phase can be used to coat core particles to form microcapsules. An example would be the precipitation of ethyl cellulose from cyclohexane by the addition of polyethylene.

(v) Interfacial Polymerization

In this technique, two reactants, each dissolved in a mutually immiscible liquid, diffuse to the interface between the two liquids where they react to form a capsule wall. An example of such capsule formation would occur if a mixture of Sebacoyl chloride dissolved in an oil phase was emulsified into an aqueous phase containing ethylenediamine.

As can be seen from the above description various different classes of polymers are capable of forming particles that can be used for pharmaceutical agent delivery.

The process of cross-linking of particles according to the invention is effected by reaction between carboxyl, hydrazidyl, amino and/or thiol groups on the polymer or polymers, which form the particle, with a spacer which comprises two or more carboxyl, hydrazidyl, amino and/or thiol groups groups, with the reaction typically being catalyzed by the presence of at least one carbodiimide. Preferred cross-linking reactions include: generation of hydrazide bonds between a hydrazide and a carboxyl group; generation of an amide between an amine and a carboxyl group; generation of a thioester between a carboxyl group and a thiol group; and generation of a disulfide between two thiol groups. It will be clearly understood by a person skilled in the art that if the polymer or polymers of the particle system chosen do not include reactive carboxyl, hydrazidyl, amino and/or thiol groups, they will need to be chemically modified in order to do so. In a typical reaction a polymer containing carboxyl groups can be substituted with hydrazidyl groups by the reaction of the polymer with a dihydrazidyl spacer and a suitable carbodiimide (See example 7 and 8, and Russell-Jones et al., *Bioconjugate Chemistry*, 6, 459–465).

Polymers suitable for use in the invention include, but are not limited to: poly-amino acids such as polyglutamic acid, polyaspartic acid, and polylysine; poly(N-acylhydroxypropine esters; polysebacic acid; polyfumaric acid; polylactic acid; polyglycolic acid; polylactic-co-glycolic acid; carboxymethylcellulose; gum arabic; alginate; polyphosphate; heparin; gelatin; copolymers of sebacic acid and fumaric acid; copolymers of biscarboxyphenoxypropane and sebacic acid; poly(carboxyphenoxyacetic) acid; poly-(carboxyphenoxyvaleric) acid; poly-$\epsilon$-caprolactone and related polyesters (poly-$\epsilon$-caprolactone-co-$\delta$-valerolactone; poly-$\epsilon$-caprolactone-co-DL-lactic acid; hyaluronic acid; chitin; chitosan; dextran; carboxy-dextran; collagen; albumin; fibrinogen; and other naturally occurring polymers.

Scheme 1 shows an example of a reaction scheme contemplated by the present invention. In this scheme the tricarboxylic acid, citric acid, first is reacted with a 2 fold molar excess of EDAC and NHS. The resultant disuccinimidyl ester is then reacted with an adipylhyrazide-modified polymer to form a covalently cross-linked polymer (See example 8).

Scheme 1

Poly[glu-co-adipylhydrazideglu]

Citric acid

Citric acid bis modified Poly[glu-co-adipylhydrazidegl

-continued

The following scheme 2 shows another example of a general reaction scheme contemplated by the present invention. In scheme 2 the carboxylic acids on the polymer are reacted with EDAC in the presence of ½ Mole equivalent of adipyldihyrazide to form a covalently cross-linked polymer (See example 3).

Scheme 2

-continued

Bis modified adipylhydrazide-polyglutamic acid

According to the present invention, there are no particular limitation to the type of carbodiimide that can be used within the present invention, although some particularly preferred carbodiimides are N-ethyl-N'-(3-dimethylaminopropyl)-carbodiimide (known as EDC or EDAC), NN'-dicyclohexylcarbodiimide (DCC), N'-diisopropyl-carbodiimide, N'N'-di-tert-butylcarbodiimide 1-cyclo-hexyl-3-(4-diethylaminocyclohexyl)carbodiimide, 1,3-di-(4-diethylaminocyclo-hexyl)carbodiimide, 1-cyclohexyl-3-(-diethylaminoethyl)carbodiimide, 1-cyclohexyl-1-cyclohexyl-3-(2-morphonlinyl-(4)-ethyl)carbodiimide 1-cyclohexyl-3-(4-diethyl-aminocyclohexyl)carbodiimide (Sheehan et al, *J. Org. Chem.*, 21, 439–441 (1956)). Indeed any 'coupling agent' can be used that generates an active ester e.g. BOP, PyBOP, TSTU, HBTU, TBTU, HBPyU, DPPA, IIDQ, EEDQ. These coupling agents are well known in the field of peptide synthesis.

The dihydrazide spacers comprehended by the invention include, but are not limited to, those which accord with general formula I, as follows:

$$NH_2NHCO-R-CONHNH_2 \quad \text{Formula I}$$

wherein R represents a direct bond, or a straight, branched chain or cyclic alkyl, alkenyl, alkynyl or aryl. R preferably contains up to 10 carbon atoms.

Preferred dihydrazides are selected from, but not limited to: oxalic dihydrazide, malonic dihydrazide, malic dihydrazide, norbornene dihydrazide, Phthalic dihydrazide, tartaric dihydrazide succinic dihydrazide, glutaric dihydrazide, adipic dihydrazide, maleic dihydrazide, fumaric dihydrazide or butadienoic dihydrazide. Hydrazine also may be used.

Carboxylic acid spacers which can be utilized according to the present invention include: malonic acid, maleic acid, citric acid, glutamic acid, aspartic acid, succinic acid, adipic acid, glutaric acid, ,dimethylglutaric acid, oxalic acid, fumaric acid, phthalic acid, tartaric acid, isophthalic acid, terephthalic acid and the branched alkyl derivatives thereof.

It also is possible for the spacer to include more than two carboxyl, hydrazidyl, amino and/or thiol groups, or even combinations of carboxyl, hydrazidyl, amino and/or thiol groups, depending upon the nature of the reactive groups present on the polymer/s. That is, if only carboxyl reactive groups are present on the polymer/s then a spacer comprising only hydrazidyl, amino, or thiol reactive groups may be employed, and vice versa. If the polymer(s) include, for example, both carboxyl and hydrazidyl groups it may be appropriate for the spacer also to comprise both of those reactive groups.

In general terms, the conditions that must be employed in effecting the cross-linking reaction are simply to provide approximately molar equivalents of the spacer and carbodiimide, depending upon the level of cross-linking that is required. It is then necessary to leave the reaction for between about two and 24 hours, preferably at least four hours, in order for the cross-linking to progress to completion. The cross-linked encapsulating particle can be recovered by dialysis against distilled water, or other suitable buffers such as PBS, saline, Hepes, etc.

The pharmaceutical agent can be incorporated within the particle at the time of formation of the particle, preferably by including the pharmaceutical agent within the mixture of components required to produce the particle. Alternatively, in cases such as the formation of nanoparticles via polyelectrolyte complexation, the pharmaceutical agent can be included in either the polycation or polyanion phase, depending upon its solubility, and the mixture can be slowly added to the precipitating phase (See example 1 and 2)

In a preferred embodiment of the invention the spacer includes a biodegradable linkage that can be degraded in a controlled manner under particular circumstances. For example, it is possible to incorporate into the spacer linkage units that will be cleaved in a defined environment such that the biodegradable linkage will be cleaved in order that the particle releases its entrapped pharmaceutical agent. These biodegradable linkages can be tailored specifically to enable cleavage of the linkage in the desired environment. Examples of some biodegradable linkages include disulphide bonds, azo groups and esters that can be cleaved under defined conditions. Suitable thiol-cleavable linkers include cystamine, cystine, and oxidized glutathione, the latter two of which can be activated with NHS and a carbodiimide and then used to cross-link hydrazidyl groups. Other thiol-cleavable cross-linkers which can be reacted directly with pendant hydrazidyl groups include, amongst others, Bis-[β-(4-azidosalicylamido)ethyl]disulfide, Dithiobis-(succinimidyl propionate), Dimethyl 3,3'-dithiobispropionimidate, 3,3'-Dithiobis(sulfosuccinimidyl propionate), Sulfosuccinimidyl 2-(m-azido-o-nitrobenzamido)ethyl-1,3'-dithiopropionate, N-Succinimidyl 6-(4'-azido-2'-nitrophenyl-amino) hexanoate and Sulfosuccinimidyl-2-(p-azido-salicylamido) ethyl-1,3-dithio-propionate.

Suitable esterase cleavable linkages include those formed from the 2-aminoethyl esters of the known amino acids, including the 2-aminoethyl ester of glycine, 2-aminoethyl ester of phenylalanine, and their disuccinimidyl derivatives, including N,N'-disuccinimidyl-(2-amino-2-benzyl-ethanoate, N,N'-dissuccinimidyl-2-amino-ethyl-ethanoate, and ethylene glycolbis[succinimidylsuccinate]

In accordance with another embodiment of the present invention it is possible for the cross-linked particles according to the invention to be linked to compounds (hereinafter referred to as "targeting compounds") which are actively absorbed across the gastrointestinal mucosa or bound to intestinal epithelial cells. For example, the particles according to the invention could be linked to vitamin $B_{12}$ or an analog thereof which will allow them to bind to intrinsic factor (IF), allowing the complex to be actively taken up from the intestine. Use of such targeting compounds is described in WO 87/02251, PCT/AU94/00273 and PCT/AU94/00274, which are incorporated herein by reference in their entirety.

The particles according to the invention also can be linked to viral adhesins, bacterial pili, toxin binding subunits, haemagglutinins, lectins or bacterial invasins which are generally present on the surfaces of bacteria and viruses and which are capable of specific binding to the intestinal epithelium. Binding to these agents therefore results in intestinal epithelial targeting (to delay transit of pharmaceutical agents down the intestine), or it can result in eliciting uptake and transcytosis of the targeting molecule and attached pharmaceutical across the intestinal epithelial cell wall.

Some examples of bacterial adhesins include proteins isolated from various Streptococcal species such as the IgA binding proteins (ARP2, ARP4, bac; Fischetti,. *ASM News*, 62, 405–410 (1996)), the IgA binding protein from Group B streptococci (Russell-Jones et al., 1984); protein antigens of Group B streptococci with special reference to the ibc antigens, Russell-Jones et al, *J. Exp. Med.*, 160, 1476–1484 (1984); fibrinogen binding proteins (Mrp4, Sfb, PrtF, fnbA, fnbB, FnBP, FnBp; Fischetti, 1996, ibid), as well as the collagen binding factor (cna) and clumping factor (clfA) from *S. aureus*.

Other structures shown to be responsible for adhesion of bacteria to epithelial surfaces are the filamentous surface adhesins or pili. These adhesins include the K88, K99 (Mouricout, et al. *Infect. Immun.*, 58, 98–106 (1990)), F41 and 987P pili found on *E. coli* inhabiting neonatal calves and piglets, the CFA1 and CFAII pili found on *E. coli* causing diarrhoea in human, and *Pseudomonas aeruginosa* PAK pilus (Irvin et al.,. *Infect. Immun.*, 57, 3720–3726 (1989)) Doig et al., *Infect. Immun.*, 58, 124–130 (1990)). There is also the type "P" pili isolated from *E. coli* strains associated with human pyelonephritis (Isberg,. *Science*, 252, 934–938 (1991)). Type I and type 2 fimbriae found on *A. viscosis* and *A. naeslundii* (respectively) also have potential roles in adherence and subsequent internalization of these bacteria (Fischetti, 1996, Ibid). Similarly, a 36 kDa protein on the surface of *N. gonorrhoeae* has been implicated in the binding of these organisms to surface lactosylceramides on human epithelial cells and may be responsible of uptake of these organisms by the epithelial cells (Paruchuri, et al., *Proc. Natl. Acad. Sci. USA*, 87, 333–337(1990)).

Many bacteria possess surface structures apart from pili that have been shown to be responsible for the epithelial invasion of these bacteria, known as bacterial invasins, which could be used according to the invention. For instance, Internalin, a surface protein encoded by the inlA gene of *L. monocytogenes* is responsible for internalization of Listeria within intestinal epithelial cells (Cossart, *J. Cell. Biochem. Suppl.* B001, pp 36 (1994)) Falkow *Cell*, 65, 1099–1102 (1991)); Mengaud et al., *Cell*, 84, 923–932 (1996)) Lingnau et al., *Infect. Immun.*, 63; 3896–3903 (1995)); Drevets et al., *Infect. Immun.*, 63; 4268–4276 (1995)). Internalization of Listeria is triggered following binding of intenalin to E-cadherin on epithelial cells (Falkow, 1991, ibid; Mengaud, et al., 1996, ibid). A protein with similar function to internalin is found on the surface of *Yersinia pseudotuberculosis;* this protein, invasin, is a 986 amino acid protein located in the *Y. pseudotuberculosis* outer membrane (Falkow, (1991), ibid; Isberg (1985) ibid. A single genetic locus encoded by *Yersinia pseudotuberculosis* permits invasion of cultured animal cells by *Escherichia coli* K-12). Expression of this protein on the surface of other gram negative bacteria such as *E. coli* K12 enables these cells to efficiently attach to and become internalized by epithelial cells (Falkow, (1991), ibid; Isberg et al (1985), ibid. Similarly latex particles coated with internalin are internalized by cultured mammalian cells. Isberg, (1991). A second protein from *Y. pseudotuberculosis,* the ail gene product, is responsible for binding of these organisms to many eukaryotic cells but only promotes uptake in a few cell types. Id.

Other structures/proteins suitable for linkage to the particles of the invention, include surface proteins from many viruses that are known to gain access to the intestinal or respiratory epithelium following binding of surface structures on the virus known as viral haemagglutinins. Such specific binding proteins have been shown on the surface of rotaviruses (VP7), adenoviruses, Norwalk virus, (Fukuhara et al,. *J. Virol.,* 62, 2209–2218 (1988)); Yolken, in Lennette (Ed.) Vol. 6; 273–291 (1985)). Similarly surface haemagglutinins also have been implicated in inducing acid-induced fusion of viruses to membranes following initial binding and uptake of influenza (Wharton et al, *J. Biol. Chem.,* 263; 4474–4480 (1988)).

Other haemagglutinin molecules exist on the surface of viruses such as rotavirus, which aid in the binding, internalization and transcytosis of these viruses across intestinal epithelial cells (Keljo et al., *J. Ped. Gastroenterol. Nutrition,* 7, 249–256 (1988)). Evidence suggests, however, that following binding of some viruses to the endocyte, the surface haemagglutin may be cleaved to yield a fusogenic protein which in turn enables the virus to enter the cell by direct cell membrane penetration, rather than by endocytosis (Kaljot et al., *J. Virol,* 62, 1136–1144 (1988)); Fukuhara, et al., (1988), ibid). Such molecules may have some utility in targeting pharmaceuticals to intestinal epithelial cells, but may not be suitable for delivery of the pharmaceutical to the circulation as the endocytosed material may not be transcytosed.

Apart from the mucosal uptake and transport of adhesins such as pili and viral haemagglutins, it has also been found that it is possible to covalently link molecules to the binding subunits of various toxin and plant lectins and to elicit uptake of the linked molecules following oral administration. Toxins of most relevance to initiate receptor-mediated uptake according to the invention are those that consist of an $AB_n$ subunit structure in which the A subunit is responsible for toxicity, while the B subunit functions as the specific binding unit of the toxin. These toxins include the cholera toxin-like molecules such as *E. coli* heat-labile toxin, cholera toxin, *Campylobacter jejuni* heat-labile toxin, *C. botulinum* C2 toxin, tetanus toxin, diphtheria toxin and *Pseudomonas exotoxin A* (Sears et al,. *Microbiol. Rev.* 60, 167–215 (1996)); Waksman et al, *Biochem. Biophys. Acta.,* 604, 249–296 (1980), verotoxin, Shiga-toxin (Okerman, *Veterinary Microbiol.,* 14, 33–46 (1987)). All of these toxins share a common property in that they must first bind-to and then cross membranes to exert their toxic activity. It is the ability of these toxins to bind to and be internalized by epithelial cells, which makes these molecules suitable vehicles for transporting molecules into and across epithelial cells.

A number of plant toxins of the general structure AB also have been identified to have the potential to bind to cells and be internalized, and are suitable molecules for targetting according to the invention. All of these toxins are active orally and as such have the ability to bind to and be internalized by enterocytes. These toxins include ricin, abrin, viscumin, modeccin and volkensin that bind to D-galactose (Stirpe et al., *FEBS,* 195, 1–8 (1986))). Other A-B toxins which could potentially bind to intestinal epithelial cells and cause uptake include botulinum toxin (from *C. botulinum*) (Blaustein et al., *FEBS,* 225, 115–120(1987)).

Importantly, this invention also relates to a method of controlled drug release within a patient, which patient is administered a composition comprising a pharmaceutical agent which is entrapped or encapsulated by a cross-linked particle according to the invention. In its broadest sense, this method can be used for the therapy, prophylaxis or diagnosis of any vertebrate animal, although it is preferred that the animal concerned is a mammal. Particularly preferred are laboratory animals such as mice, guinea pigs, rabbits, domestic animals such as cats and dogs, farm animals such as horses, cattle, sheep, goats, pigs, captive wild animals such as lions, tigers, elephants or primates such as humans, chimpanzees, baboons and apes.

The effective amount of the pharmaceutical agent delivered when provided in combination with the cross-linked particles of the invention depends upon numerous factors. The nature of these factors will readily be apparent to a person skilled in the art. For example, relevant factors include the type, age and sex of the vertebrate animal concerned, the disorder that the animal is suffering from or is prone to suffer from, the height and weight of the animal, and the type of pharmaceutical agent that is being delivered. The dose also will depend upon whether the cross-linked particles are linked to other agents that aid uptake, as well as upon the stability of the particle and the level of control over release of the entrapped or encapsulated pharmaceutical agent, which will be related to the nature and extent of cross-linkage. When all of these factors are taken into consideration by a person skilled in the art, the appropriate dose can be determined. Routine dosage regimens that can be used to determine the optimum or appropriate dosage of the pharmaceutical agent are well known to those of skill in the art.

The compositions according to the invention also may be administered in conjunction with one or more pharmaceutically suitable carriers and/or excipients. The nature of the carrier or excipient substance will depend upon factors such as the route of administration, the nature of the cross-linked particle, and the nature of the pharmaceutical agent concerned. A complete discussion of appropriate pharmaceutical carriers and excipients is provided in the HANDBOOK OF PHARMACEUTICAL EXCIPIENTS, Second Edition, 1994, Wade and. Weller (Eds.), The Pharmaceutical Press, London, which is incorporated herein by reference in its entirety.

As described above, the compositions according to the invention can be administered via either enteral or parenteral routes of administration. In a preferred embodiment of the invention, administration is via the oral route although, for example, rectal administration or direct administration to the stomach or small intestine also is possible. In addition, the compositions according to the invention can be administered intramuscularly, intraperitoneally, subcutaneously, optically, aurally, vaginally, topically, directly into an organ or via other parenteral means. The skilled artisan will appreciate that administration via these means requires that the composition be provided in a suitable dosage form with appropriate carriers and/or excipients, as described in the Handbook of Pharmaceutical Excipients, supra.

The present invention, thus generally described, will be understood more readily by reference to the following examples, which are provided by way of illustration and are not intended to be limiting of the present invention.

EXAMPLE 1

Synthesis of Nanoparticles Containing Insulin via Polyelectrolyte Complexation Using Gelatin and Carboxymethyl Cellulose Carboxymethyl cellulose (low viscosity, 50–200 cps) was dissolved at 5% in distilled water (DW) and the pH adjusted to pH 3.9 with 1 M HCl. Gelatin (Bloom 175) was dissolved at 5% in DW and the pH adjusted to 3.9 with 1 M HCl. Insulin was dissolved at 20 mg/ml in 20 mM HCl and 400 µl added to 4.0 ml gelatin which had been heated to 60° C. The insulin/gelatin mix was slowly added to 2.0 ml of carboxymethyl cellulose (5%) whilst stirring vigorously. Stirring was continued for 15 minutes at which time 12 ml DW was added. Adipyl hydrazide (48 mg at 100 mg/ml in DW) was added to the solution followed by 48 mg EDAC (100 mg/ml). The solution was stirred for more than 4 hours, followed by exhaustive dialysis against DW.

EXAMPLE 2

Preparation of Gelatin/Polyglutamate Nanoparticles which Contain Insulin via Polyelectrolyte Complexation Polyglutamate (17,500 MW) was dissolved at 0.25% in distilled water (DW) and the pH adjusted to pH 3.9 with 1 M HCl. Gelatin (Bloom 175) was dissolved at 1.0% in DW and the pH adjusted to 3.9 with 1 M HCl. Insulin was dissolved at 20 mg/ml in 20 mM HCl and 350 µl added to 4.0 ml gelatin which had been heated to 60° C. The insulin/gelatin mix was slowly added to 4.0 ml of 0.25% Polyglutamate, whilst stirring vigorously. Stirring was continued for 15 minutes at which time 8 ml DW was added. Adipyl hydrazide (5 mg at 100 mg/ml in DW) was added to the solution followed by 5 mg EDAC (100 mg/ml). The solution was stirred for more than 4 hours, followed by exhaustive dialysis against DW.

EXAMPLE 3

Preparation of Gelatin/alginate Nanoparticles which Contain Insulin via polyelectrolyte Complexation Sodium alginate (low viscosity, 250 cps) was dissolved at 1.25% in distilled water (DW) and the pH adjusted to pH 3.9 with 1 M HCl. Gelatin (Bloom 175) was dissolved at 1.25% in DW and the pH adjusted to 3.9 with 1 M HCl. Insulin was dissolved at 20 mg/ml in 20 mM HCl and 1.0 ml added to 5.0 ml gelatin which had been heated to 60° C. The insulin/gelatin mix was slowly added to 10.0 ml of alginate (1.25%), whilst stirring vigorously. Stirring was continued for 15 minutes at which time 15 ml DW was added. Adipyl hydrazide (60 mg @ 100 mg/ml in DW) was added to the solution followed by 60 mg EDAC (100 mg/ml). The solution was stirred for more than 4 hours, followed by exhaustive dialysis against DW.

EXAMPLE 4

Figure 1:
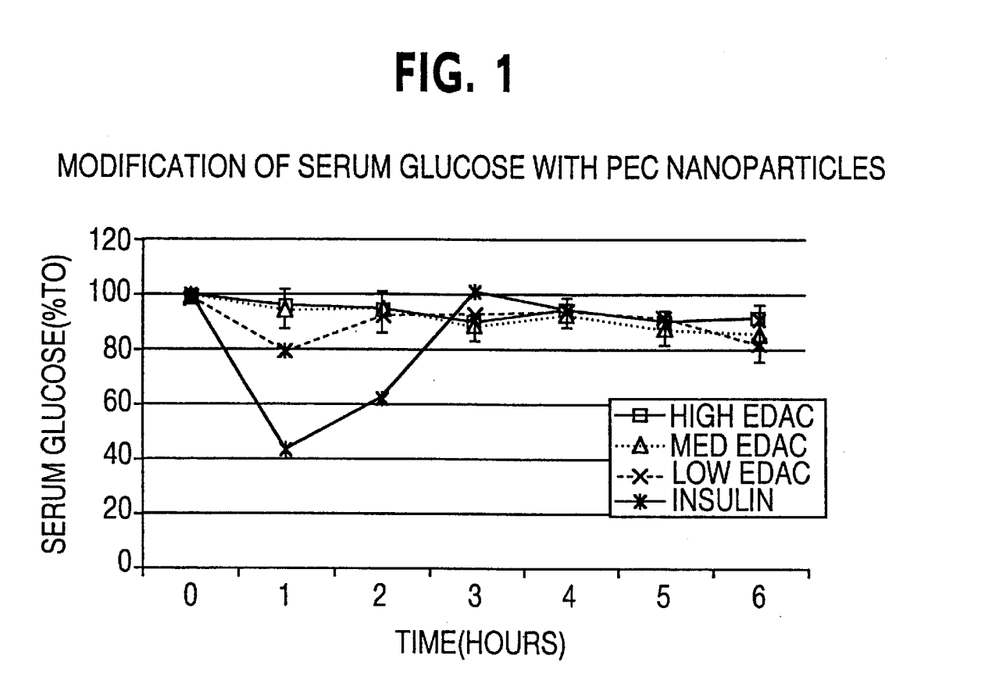
FIG. 1 shows a plot of the change in serum glucose levels in male Wistar rats following intravenous administration of insulin and insulin entrapped within a cross-linked particle formed from gelatin and carboxymethyl cellulose (CMC). The plot shows percentage serum glucose concentration (relative to serum glucose concentration at time 0), versus time. Blood analysis was conducted at 0, 1, 2, 3, 4, 5 and 6 hours post-administration. The rats are administered either highly cross-linked particles, moderately cross-linked particles, particles with a low degree of cross-linking or an insulin control. Each of the rats was administered either 100 μg of insulin or a preparation of particles containing 100 μg of insulin.

In vivo Release of Insulin from Gelatin/CMC Polyelectrolyte Complex Nanoparticles Following Intravenous Injection in Rats Male Wistar rats were placed in a restraining apparatus and a blood sample obtained from the tail vein of the conscious rats. The rats were then injected intravenously with a saline solution containing either 100 µg dose of insulin or a preparation of gelatin/CMC nanoparticles containing 100 µg of insulin. At 60, 120, 180, 240 and 300 minutes following injection the rats were from the tail vein. The collected blood was allowed to clot at 4° C., after which the serum was separated from the clot via centrifugation. Blood glucose levels were obtained using a standard glucose assay such as that sold by Sigma (#GAGO-20). Results are shown in FIG. 1.

EXAMPLE 5

Figure 2:
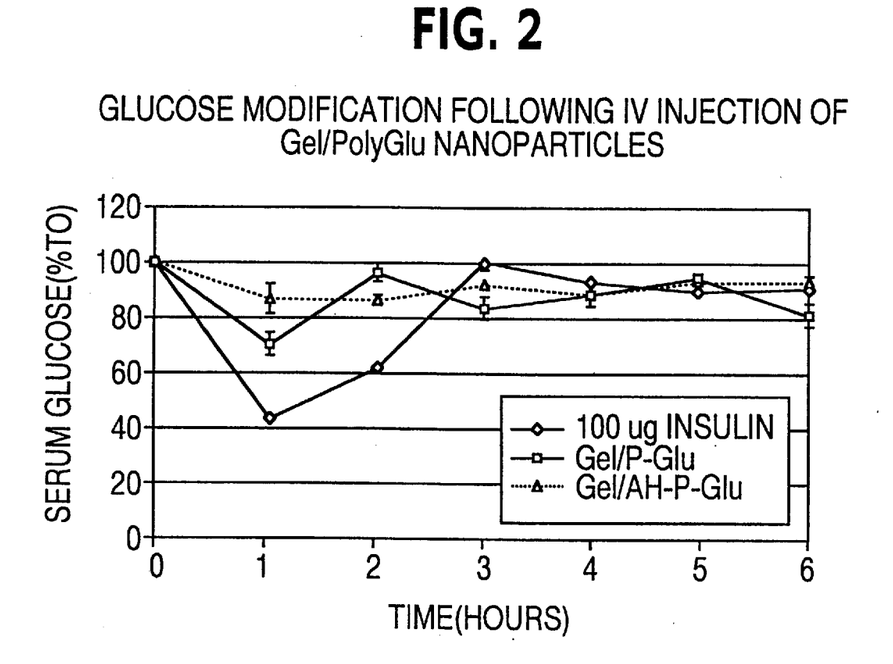
FIG. 2 shows a plot of the change in serum glucose levels of male Wistar rats following intravenous administration of insulin and of insulin entrapped within a cross-linked particle formed from gelatin and polyglutamic acid [Gel/P-Glu] or gelatin and adipylhydrazidyl [Gel/AH-P-Glu]. The plot shows percentage serum glucose concentration (relative to serum glucose concentration at time 0), against time. Blood analysis was conducted at 0, 1, 2, 3, 4, 5 and 6 hours post-administration. Each of the rats was administered either 100 μg of insulin or a preparation of particles containing 100 μg of insulin.

Modification of Insulin Release from Polyelectrolyte Complex (PEC) Nanoparticles by Varying the Concentration of EDAC and Adipyl Hydrazide The rate of release of insulin from PEC nanoparticles was modified by altering the concentration of EDAC and adipyl hydrazide used in cross-linking the PEC nanoparticles formed by any of the above procedures. Release rates were increased by reduction in concentration of the cross-linkers; conversely, increasing the concentration of cross-linkers decreased the release rates (See FIG. 2).

EXAMPLE 6

Preparation of Hydrazidyl-polyglutamic Acid

Polyglutamate was dissolved at 25.8 mg/ml in DW. Adipyl hydrazide (87 mg/ml in DW) was added to the polyglutamate at 2:5 volume:volume ratio. Solid EDAC (4 mg/ml of Polyglutamate) was added to the solution and allowed to react for 2 hours. The resultant solution was dialysed extensively against DW and lyophilized.

EXAMPLE 7

Preparation of Hydrazidyl-carboxymethyl Cellulose

Carboxymethyl cellulose was dissolved at 25 mg/ml in DW. Adipyl hydrazide (87 mg/ml in DW) was added to the polyglutamate at 2:5 volume:volume ratio. Solid EDAC (4 mg/ml of Carboxymethyl cellulose) was added to the solution and allowed to react for 2 hours. The resultant solution was dialysed extensively against DW and lyophilized.

EXAMPLE 8

Preparation of PEC Nanoparticles Containing Insulin and Formed with Adipylhydrazidyl-polyglutamic Acid and Gelatin Adipyl-hydrazidyl-Polyglutamate was dissolved at 2.5 mg/ml in DW and the pH adjusted to pH 3.9 with 1.0 M HCl. Insulin was dissolved at 20 mg/ml in 20 mM HCl and added to a solution of Gelatin (Bloom 175; 10 mg/ml in DW, pH 3.9) which had been heated to 60° C., to give a solution of 0.8 mg/ml insulin in gelatin. The solution was added to an equal volume of a warm solution (60 C.) of adipyl-hydrazidyl-Polyglutamate while stirring rapidly. After stirring for 15 minutes the solution was diluted 1:3 in DW. Citric acid (100 mg/ml) was mixed with an equal weight of NHS (100 mg/ml in acetone) and the NHS-ester formed by reaction with a 2-fold weight excess of EDAC. Following 10-minute activation the $NHS_2$-citrate was added to the microparticles at a weight equal to that of the adipyl-hydrazidyl-Polyglutamate. The reaction was allowed to proceed overnight, after which the material was dialyzed extensively against DW.

EXAMPLE 9

Preparation of PEC Nanoparticles Containing Insulin and Formed with Hydrazidyl-carboxymethyl Cellulose and Gelatin Adipyl-hydrazidyl-Carboxymethyl cellulose was dissolved at 25 mg/ml in DW and the pH adjusted to pH 3.9 with 1.0 M HCl. Insulin was dissolved at 20 mg/ml in 20 mM HCl and added to a solution of gelatin (Bloom 175, 8 mg/ml in DW, pH 3.9) to give a solution of 0.8 mg/ml insulin in gelatin. The solution was added to half volume of a warm solution (60° C.) of adipyl-hydrazidyl-Carboxymethyl cellulose while stirring rapidly. After stirring for 15 minutes the solution was diluted 1:3 in DW. Citric acid (100 mg/ml) was mixed with an equal weight of NHS (100 mg/ml in acetone) and the NHS-ester formed by reaction with a 2-fold weight excess of EDAC. Following 10 minute activation the $NHS_2$-citrate was added to the microparticles at a weight equal to that of the adipyl-hydrazidyl-Carboxymethyl cellulose. The reaction was allowed to proceed overnight, after which the material was dialyzed extensively against DW.

EXAMPLE 10

Preparation of 2-aminoethyl-2-aminoethanoate (AEAE)

(a) Coupling of Boc-glycine with Boc-ethanolamine

Boc-glycine (12.0 g, 0.068 mol) and carbonyl diimidazole (12.1 g, 0.074 mol) were dissolved in DMF (50 mL) with vigorous evolution of $CO_2$ and the solution stirred at room temperature for 1 h. A solution of Boc-ethanolamine (10.0 g, 0.062 mol) in DMF (10 mL) was added dropwise to the active ester solution followed by DIEA (11.9 mL, 8.80 g, 0.068 mol) and stirring was continued at room temperature overnight. The solution was poured into water (200 mL) and extracted with ether (3×75 mL), washed with saturated sodium hydrogen carbonate solution (1×100 mL), dried (MgSO$_4$) and the solvent removed to give the product (18.1 g, 92 %) as a colourless oil which was used without further purification.

(b) Removal of Boc protecting group and succinylation

The crude di-Boc ester (22.9 g, 0.072 mol) was dissolved in trifluoroacetic acid (20 mL) at 0° with the vigorous evolution of $CO_2$ and the solution stirred at 0° for 1 h. The trifluoroacetic acid was removed under reduced pressure, the residue dissolved in acetonitrile (30 mL) and the solvent removed again. The crude bis-TFA salt was dissolved in THF (20 mL) and solid anhydrous potassium carbonate (20 g) was added and the mixture stirred at room temperature for 1 h. The solution was dried (Na2SO$_4$) and the solution filtered into a solution of succinic anhydride (22.7 g, 0.23 mol) in THF (120 mL). DIEA (30 mL, 22.3 g, 0.17 mol) was added to give a basic solution and stirring was continued at room temperature. At 1 h intervals, two aliquots of DIEA (5 mL, 3.70 g, 0.029 mol) were added and stirring was continued for 24 h. Most of the THF was removed under reduced pressure and the suspension was poured into two phase saturated sodium hydrogen carbonate solution (200 mL) and ethyl acetate (100 mL). The organic layer was removed and the aqueous layer was reextracted with ethyl acetate (100 mL), the aqueous layer was acidified to pH~1 with hydrochloric acid (10 M) and extracted with ethyl acetate (3×150 mL), dried (Na$_2$SO$_4$) and the solvent removed. The residue was suspended in ether (50 mL), cooled to 0° and filtered to give the product (6.01 g, 25 %) as minute needles.

(c) Preparation of dihydrazidyl ester cross-linker

To a solution of the foregoing diacid (987 mg, 3.10 mmol) in DMF (20 mL) was added PyBOP (3.72 g, 7.15 mmol) and t-butyl carbazate (950 mg, 7.19 mmol) followed by DIEA (2.20 mL, 1.65 g, 0.013 mol) and stirring was continued at room temperature overnight. The solution was poured into saturated sodium hydrogen carbonate solution (100 mL) and extracted with ethyl acetate (3×50 mL), dried (MgSO$_4$) and the solvent removed to leave an oil which was dissolved in TFA (10 mL) and stirred at room temperature for 1 h. Ethanol was added (20 mL) and the solvents removed under reduced pressure to give the dihydrazide as a yellow oil (506 mg, 47%).

EXAMPLE 11

Preparation of 2-aminoethyl-2-amino-2-benzyl-ethanoate(AEABE)

(a) Coupling of Boc-phenylalanine with Boc-ethanolamine

Boc-phenylalanine (15.7 g, 0.059 mol) and carbonyl diimadazole (10.1 g, 0.062 mol) were dissolved in DMF (60 mL) with vigorous evolution of $CO_2$ and the solution stirred at room temperature for 1 h. A solution of Boc-ethanolamine (9.35 g, 0.058 mol) in DMF (10 mL) was added dropwise to the active ester solution followed by DIEA (12.0 mL, 8.9 g, 0.069 mol) and stirring was continued at room temperature overnight. The solution was poured into water (200 mL) and extracted with ether (3×75 mL), washed with saturated sodium hydrogen carbonate solution (1×100 mL), dried ($MgSO_4$) and the solvent removed to give the product (18.13 g, 92%) as a colourless oil which eventually solidified and was used without further purification.

(b) Removal of Boc protecting group and succinylation

The crude di-Boc ester (9.83 g, 0.024 mol) was dissolved in trifluoroacetic acid (20 mL) at 0° with the vigorous evolution of $CO_2$ and the solution stirred at 0° for 1 h. The trifluoroacetic acid was removed under reduced pressure, the residue dissolved in acetonitrile (30 mL) and the solvent removed again. The crude bis-TFA salt was dissolved in THF (20 mL) and solid anhydrous potassium carbonate (20 g) was added and the mixture stirred at room temperature for 1 h. The solution was dried ($Na_2SO_4$) and the solution filtered into a solution of succinic anhydride (4.98g, 0.050 mol) in THF (30 mL). DIEA (20 mL, 14.8 g, 0.11 mol) was added to give a basic solution and stirring was continued at room temperature for 24 h. Most of the THF was removed under reduced pressure and the suspension was poured into two phase saturated sodium hydrogen carbonate solution (200 mL) and ethyl acetate (100 mL). The organic layer was removed and the aqueous layer was re-extracted with ethyl acetate (100 mL), the aqueous layer was acidified to pH~1 with hydrochloric acid (10 M) and extracted with ethyl acetate (3×150 mL), dried ($Na_2SO_4$) and the solvent removed. The residue was recrystallised from ethyl acetate/hexane to give the product (2.04 g, 22 %) a colourless powder.

EXAMPLE 12

Figure 3:
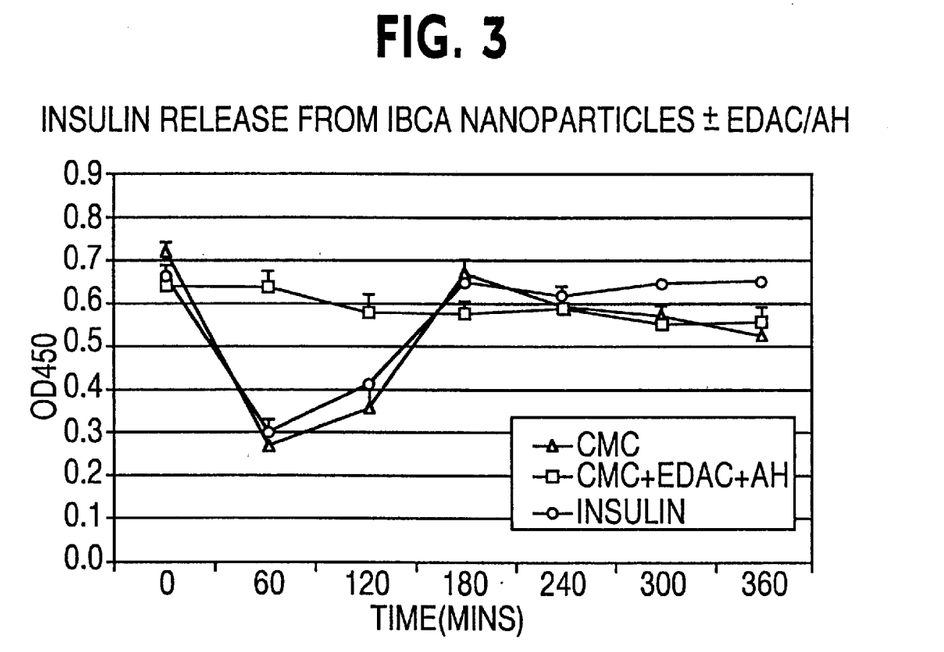
FIG. 3 shows the effect on the glucose levels in rats upon administration of insulin-containing particles. Cross-linking with EDAC and AH greatly reduced the rate of release of insulin from the particles.

Synthesis of Nanoparticles Containing Insulin Using Isobutylcyanoacrylate (IBCA) and Carboxymethyl Cellulose Insulin was dissolved at 100 mg/ml in 0.1 M HCl. An aliquot of insulin (120 μl) was mixed with an equal volume of miglyol. The solution was vortexed rapidly, 12 ml ethanol was added and the solution vortexed again. Finally, 120 μl IBCA was added and the solution slowly dripped into 24 ml of 0.25% PE6800. After 15 minutes 6 ml of 0.25% CMC was added to the solution which was allowed to stir for a further 90 minutes. The solution was then split into two equal volumes and 24 mg of adipyldihydrazide (AH) plus 48 mg EDAC was added to one solution. The particles were allowed to cross-link overnight before being tested in rats. As can be seen in FIG. 3. Addition of EDAC and AH to the nanoparticles greatly reduced the rate of release of insulin, as judged by modification of serum glucose.

EXAMPLE 13

Figure 4:
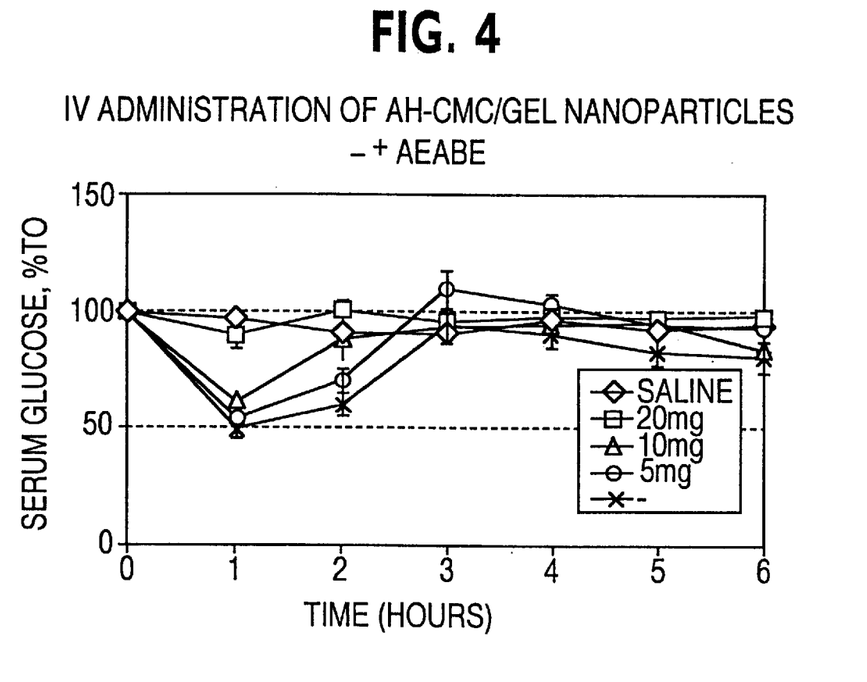
FIG. 4 shows the effect of increasing quantities of esterase-cleavable cross-linker on the in vivo rate of release of insulin from AH-CMC nanoparticles.

Preparation of Polyelectrolyte Nanoparticles Containing Insulin Cross-linked with Esterase-cleavable AEABE Adipyl-hydrazidyl-Carboxymethyl cellulose was dissolved at 2.5 mg/ml in DW and the pH adjusted to pH 3.9 with 1.0 M HCl. Insulin was dissolved at 20 mg/ml in 20 mM HCl and 8 mg added to 2 ml of a solution of 2.5 mg/ml gelatin (pH 3.9). The solution was added to 16 ml of a warm solution (60° C.) of adipyl-hydrazidyl-Carboxymethyl cellulose while stirring rapidly. After stirring for 15 minutes the solution was split into 4 equal samples. AEABE (40 mg @100 mg/ml) was mixed with 30 mg NHS (100 mg/ml in DMF) and the NHS-ester formed by reaction with 60 mg EDAC. Following 10 minute activation 20, 10 and 5 mg aliquots of the $(NHS)_2$-AEABE were added to the nanoparticles. The reaction was allowed to proceed overnight, and was then tested following intravenous administration to rats. As shown in FIG. 4, addition of increasing quantities of the esterase cleavable cross-linker resulted in decreasing release of insulin in vivo.

EXAMPLE 14

Figure 5:
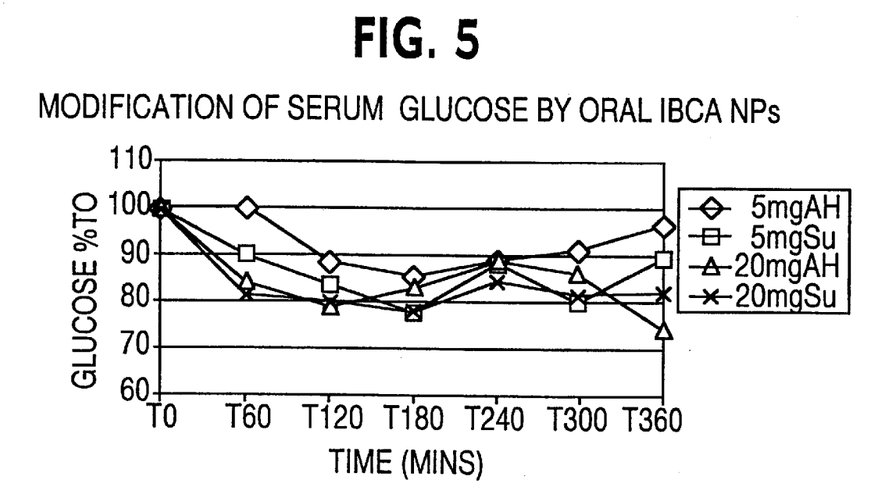
FIG. 5 shows the reduction in serum glucose level in rats following oral administration of vitamin B12-conjugated insulin-containing IBCA nanoparticles.

Oral Administration of IBCA Nanoparticles Containing Insulin Cross-linked with Esterase-cleavable AEABE Insulin was dissolved at 100 mg/ml in 0.1 M HCl. An aliquot of insulin (120 μl) was mixed with an equal volume of miglyol. The solution was vortexed rapidly, 12 ml ethanol was added and the solution vortexed again. Finally, 120 µl IBCA was added and the solution slowly dripped into 24 ml of 0.25% PE6800. After 15 minutes 6 ml of 0.25% adipyl-hydrazidyl-CMC was added to the solution which was allowed to stir overnight. The particles were then concentrated up to 22 ml. AEABE (60 mg @100 mg/ml) was mixed with 60 mg NHS (100 mg/ml in DMF) and the NHS-ester formed by reaction with 60 mg DCC (Dicyclohexylcarbodiimide, 103 mg/ml in DMF). Following 10 minute activation 5 and 40 mg aliquots of the $(NHS)_2$-AEABE were added to 11 ml aliquots of nanoparticles. The reaction was allowed to proceed overnight. The particles were then dialysed extensively against DW to remove free AEABE. Each sample was further split into 2. Adipyl-hydrazide-eVB12 (20 mg) plus 20 mg EDAC was added to one sample while TSTU-activated-eVB12 (20 mg) was added to the other sample and allowed to react for 2 hours. The samples were then dialysed against distilled water and tested following oral administration to rats. As shown in FIG. 5, all particle preparations resulted in a reduction in serum glucose for a period of 5 hours after oral administration.

As used herein, unless the context requires otherwise, the word "comprise", or variations such as "comprises" or "comprising", will be understood to imply the inclusion of a stated element or integer or group of elements or integers but not the exclusion of any other element or integer or group of elements or integers.

What is claimed is:

1. A cross-linked particle comprising at least one polymer capable of forming a particle, wherein said polymer comprises:
   (i) reactive groups selected from the group consisting of carboxyl, hydrazidyl, amino and thiol groups, covalently linked to
   (ii) a spacer having the formula $NH_2NHCO—R—CONHNH_2$,
   wherein —R— is a direct bond, or R is a straight, branched chain or cyclic alkyl, alkenyl, alkynyl or aryl group, wherein said alkyl, alkenyl, or alkynyl group contains up to 10 carbon atoms.

2. The cross-linked particle according to claim 1 wherein the spacer is selected from the group consisting of: hydrazine, oxalic dihydrazide, malonic dihydrazide, succinic dihydrazide, glutaric dihydrazide, adipic dihydrazide, maleic dihydrazide, fumaric dihydrazide or butadienoic dihydrazide, glutamic dihydrazide, aspartic dihydrazide, malic dihydrazide, tartaric dihydrazide, terephthalic dihydrazide, isophthalic dihydrazide, and phthalic dihydrazide.

3. The cross-linked particle according claim 1, wherein said spacer comprises at least one biodegradable linkage.

4. The cross-linked particle according to claim 1, wherein said particle is covalently bound to a targeting compound.

5. A composition comprising a pharmaceutical agent entrapped within a cross-linked particle comprising at least one polymer capable of forming a particle, wherein said polymer comprises:
   (i) reactive groups selected from the group consisting of carboxyl, hydrazidyl, amino and thiol groups, covalently linked to
   (ii) a spacer having the formula $NH_2NHCO—R—CONHNH_2$,
   wherein —R— is a direct bond, or R is a straight, branched chain or cyclic alkyl, alkenyl, alkynyl or aryl group, wherein said alkyl, alkenyl, or alkynyl group contains up to 10 carbon atoms.

6. The composition according to claim 5 wherein said spacer is selected from the group consisting of hydrazine, oxalic dihydrazide, malonic dihydrazide, succinic dihydrazide, glutaric dihydrazide, adipic dihydrazide, maleic dihydrazide, fumaric dihydrazide and butadienoic dihydrazide.

7. The composition according to claim 5 wherein said spacer includes at least one biodegradable linkage.

8. The composition according to claim 5 wherein said the biodegradable linkage is an ester linkage.

9. The composition according to claim 5, wherein said pharmaceutical agent is selected from the group consisting of peptide and protein pharmaceuticals, DNA, RNA,), antibodies, vaccines, imaging agents, hormones, polysaccharides, antibiotics, anticoagulants, immunomodulating agents, cytotoxic agents, steroids, decongestants, anesthetics and sedatives.

10. The composition according to claim 9, wherein said pharmaceutical agent is selected from the group consisting of calcitonin, erythropoietin, thrombopoietin, granulocyte colony stimulating factor, stem cell factor, LHRH analogs, somatostatin, insulin, interferons and plasminogen activator inhibitors.

11. The composition according to claim 5, wherein the cross-linked particle is covalently bound to a targeting compound.

12. A method of producing a cross-linked particle, comprising reacting at least one polymer capable of forming a particle with a spacer,
   wherein said polymer comprises at least two reactive carboxyl groups and wherein said spacer has the formula $NH_2NHCO—R—CONHNH_2$,
   wherein —R— is a direct bond, or R is a straight, branched chain or cyclic alkyl, alkenyl, alkynyl or aryl group, wherein said alkyl, alkenyl, or alkynyl group contains up to 10 carbon atoms;
   and where said cross-linking is achieved using a carbodiimide as a cross-linking agent.

13. The method according to claim 12 wherein said spacer is selected from the group consisting of hydrazine, oxalic dihydrazide, malonic dihydrazide, succinic dihydrazide, glutaric dihydrazide, adipic dihydrazide, maleic dihydrazide, fumaric dihydrazide and butadienoic dihydrazide.

14. The method according to claim 12, wherein said carbodiimide is selected from the group consisting of N-ethyl-N'-(3-dimethylaminopropyl)carbodiimide (known as EDC or EDAC), N,N'-dicyclohexyl-carbodiimide (DCC), N'-diisopropyl-carbodiimide, N'N'-di-tert-butylcarbodiimide 1-cyclohexyl-3-(4-diethylamino-cyclohexyl)carbodiimide, 1,3-di-(4-diethylaminocyclohexyl)carbodiimide, 1-cyclohexyl-3-(β-diethylaminoethyl)carbodiimide, 1-cyclohexyl-3-(2-morpholinyl-(4)-ethyl)carbodiimide, and 1-cyclohexyl-3-(4-diethyl-aminocyclohexyl)carbodiimide.

15. The method according to claim 12, wherein said spacer comprises at least one biodegradable linkage.

16. The method according to claim 12, wherein said cross-linked particle is covalently bound to a targeting compound.

17. A method of preparing a composition comprising a pharmaceutical agent entrapped within a cross-linked particle, wherein said cross-linked particle comprises at least one polymer capable of forming a particle, wherein said polymer comprises:
(i) reactive carboxyl groups, covalently linked to
(ii) a spacer having the formula $NH_2NHCO—R—CONHNH_2$,
wherein —R— is a direct bond, or R is a straight, branched chain or cyclic alkyl, alkenyl, alkynyl or aryl group, wherein said alkyl, alkenyl, or alkynyl group contains up to 10 carbon atoms, and
wherein said particle is formed by reacting at least one polymer with a spacer in the presence of said pharmaceutical agent, and a carbodiimide.

18. The method according to claim 17, wherein said spacer is selected from the group consisting of hydrazine, oxalic dihydrazide, malonic dihydrazide, succinic dihydrazide, glutaric dihydrazide, adipic dihydrazide, maleic dihydrazide, fumaric dihydrazide and butadienoic dihydrazide.

19. The method according to claim 17, wherein the reaction between said polymer and said spacer is catalyzed by a carbodiimide selected from the group consisting of N-ethyl-N'-(3-dimethylaminopropyl)-carbodiimide, NN'-dicyclohexyl-carbodiimide, N'-diisopropyl-carbodiimide, N'N'-di-tert-butylcarbodiimide 1-cyclohexyl-3-(4-diethylaminocyclohexyl)carbodiimide, 1,3-di-(4-diethylaminocyclohexyl)carbodiimide, 1-cyclohexyl-3-(β-diethylaminoethyl)carbodiimide, 1-cyclohexyl-3-(2-morpholinyl-(4)-ethyl)carbodiimide, and 1-cyclohexyl-3-(4-diethyl-aminocyclohexyl)carbodiimide.

20. The method according to claim 17, wherein said spacer comprises at least one biodegradable linkage.

21. The method according to claim 17, wherein said the pharmaceutical agent is selected from the group consisting of peptide and protein pharmaceuticals, DNA, RNA, antibodies, vaccines, imaging agents, hormones, polysaccharides, antibiotics, anticoagulants, immunomodulating agents, cytotoxic agents, steroids, decongestants, anaesthetics and sedatives.

22. The method according to claim 21, wherein said pharmaceutical agent is selected from the group consisting of calcitonin, erythropoietin, thrombopoietin, granulocyte colony stimulating factor, stem cell factor, LHRH analogs, somatostatin, insulin, interferons and plasminogen activator inhibitors.

23. The method according claim 17, wherein said cross-linked particle is covalently bound to a targeting compound.

24. A method of achieving controlled release of a pharmaceutical agent within a patient, comprising administering to said patient an effective amount of a composition comprising a pharmaceutical agent within a cross-linked particle, wherein said cross-linked particle comprises at least one polymer capable of forming a particle, and wherein said polymer comprises:
(i) reactive carboxyl groups, covalently linked to
(ii) a spacer having the formula $NH_2NHCO—R—CONHNH_2$,
wherein —R— is a direct bond, or R is a straight, branched chain or cyclic alkyl, alkenyl, alkynyl or aryl group, wherein said alkyl, alkenyl, or alkynyl group contains up to 10 carbon atoms.

25. The method according to claim 24, wherein said spacer is selected from the group consisting of hydrazine, oxalic dihydrazide, malonic dihydrazide, succinic dihydrazide, glutaric dihydrazide, adipic dihydrazide, maleic dihydrazide, fumaric dihydrazide and butandioic dihydrazide.

26. The method according to claim 24, wherein said spacer includes at least one biodegradable linkages.

27. The method according to claim 24, wherein said pharmaceutical agent is selected from the group consisting of peptide and protein pharmaceuticals, DNA, RNA, antibodies, vaccines, imaging agents, hormones, polysaccharides, antibiotics, anticoagulants, immunomodulating agents, cytotoxic agents, steroids, decongestants, anesthetics and sedatives.

28. The method according to claim 27, wherein said pharmaceutical agent is selected from the group consisting of calcitonin, erythropoietin, thrombopoietin, granulocyte colony stimulating factor, stem cell factor, LHRH analogs, somatostatin, insulin, interferons and plasminogen activator inhibitors.

29. The method according to claim 24, wherein said cross-linked particle is bound to a targeting compound.

\* \* \* \* \*